United States Patent
Andersson et al.

(10) Patent No.: US 11,389,180 B2
(45) Date of Patent: Jul. 19, 2022

(54) BONE FIXTURE FOR A MEDICAL PROSTHESIS

(71) Applicant: Cochlear Limited, Macquarie University (AU)

(72) Inventors: Marcus Andersson, Mölnlycke (SE); Stefan Magnander, Mölnlycke (SE)

(73) Assignee: Cochlear Limited, Macquarie University (AU)

( * ) Notice: Subject to any disclaimer, the term of this patent is extended or adjusted under 35 U.S.C. 154(b) by 278 days.

(21) Appl. No.: 16/534,284

(22) Filed: Aug. 7, 2019

(65) Prior Publication Data

US 2019/0357922 A1 Nov. 28, 2019

Related U.S. Application Data

(62) Division of application No. 14/837,091, filed on Aug. 27, 2015, now Pat. No. 10,376,269.

(Continued)

(51) Int. Cl.
*A61B 17/16* (2006.01)
*A61B 17/86* (2006.01)
(Continued)

(52) U.S. Cl.
CPC ...... *A61B 17/1655* (2013.01); *A61B 17/8635* (2013.01); *H04R 25/606* (2013.01); *A61B 2017/00876* (2013.01)

(58) Field of Classification Search
CPC . A61B 17/16; A61B 17/1655; A61B 17/8635; A61B 2017/00876; H04R 25/606
(Continued)

(56) References Cited

U.S. PATENT DOCUMENTS 4,612,915 A * 9/1986 Hough ................. H04R 25/606
600/25
5,797,914 A * 8/1998 Leibinger .......... A61B 17/8635
411/387.8
(Continued)

FOREIGN PATENT DOCUMENTS

CN 101035461 A 9/2012
WO 02/09622 A1 2/2002

OTHER PUBLICATIONS

International Preliminary Report on Patentability and Written Opinion of the International Searching Authority in counterpart International Application No. PCT/IB2015/056508, dated Jul. 20, 2017, 8 pages.

(Continued)

*Primary Examiner* — Sunita Reddy
(74) *Attorney, Agent, or Firm* — Edell, Shapiro & Finnan, LLC

(57) ABSTRACT

Presented herein is a bone fixture for a medical prosthesis. The bone fixture includes a self-drilling threaded body that is configured to be inserted into a recipient's bone. The threaded body includes a bone removal mechanism configured to cut away parts of the bone that are in the path of the threaded body and to remove portions of the cut parts of the bone, sometimes referred to herein as bone fragments, from the hole. The bone fixture also comprises a coupling section that is attached to a proximal end of the threaded body. The coupling section is configured to be positioned external to the recipient's bone and includes a connector interface that is entirely/completely proximal to the threaded body.

20 Claims, 10 Drawing Sheets

Related U.S. Application Data

(60) Provisional application No. 62/042,963, filed on Aug. 28, 2014.

(51) Int. Cl.
*H04R 25/00* (2006.01)
*A61B 17/00* (2006.01)

(58) Field of Classification Search
USPC ........... 600/25; 606/300, 311, 312; 433/167, 433/174
See application file for complete search history.

(56) References Cited

U.S. PATENT DOCUMENTS

| | | | |
|---|---|---|---|
| 5,897,319 A | 4/1999 | Wagner et al. | |
| 5,935,170 A | 8/1999 | Hakansson et al. | |
| 6,565,573 B1* | 5/2003 | Ferrante | A61B 17/863 606/308 |
| 8,080,044 B2 | 12/2011 | Biedermann et al. | |
| 8,787,608 B2 | 7/2014 | Van Himbeeck et al. | |
| 9,084,646 B2 | 7/2015 | Sevrain | |
| 9,314,286 B2 | 4/2016 | Bottlang et al. | |
| 2004/0044345 A1 | 3/2004 | DeMoss et al. | |
| 2004/0210103 A1 | 10/2004 | Westerkull | |
| 2005/0021036 A1 | 1/2005 | Whitmore et al. | |
| 2006/0004364 A1* | 1/2006 | Green | A61B 17/0642 606/232 |
| 2006/0050913 A1 | 3/2006 | Westerkull | |
| 2008/0261175 A1* | 10/2008 | Hurson | A61C 8/0025 433/173 |
| 2008/0292429 A1* | 11/2008 | Hasenbohler | A61B 17/8625 411/413 |
| 2009/0018589 A1* | 1/2009 | Smisson, III | A61B 17/863 606/301 |
| 2009/0082817 A1 | 3/2009 | Jinton et al. | |
| 2009/0136898 A1* | 5/2009 | Kim | A61B 17/1655 433/165 |
| 2010/0268313 A1 | 10/2010 | Conn | |
| 2010/0286776 A1 | 11/2010 | Andersson | |
| 2010/0292529 A1 | 11/2010 | Westerkull et al. | |
| 2012/0078035 A1 | 3/2012 | Andersson et al. | |
| 2012/0172658 A1 | 7/2012 | BJorn et al. | |
| 2012/0302822 A1 | 11/2012 | Van Himbeeck et al. | |
| 2013/0090518 A1 | 4/2013 | BJorn et al. | |
| 2014/0012334 A1* | 1/2014 | Armstrong | A61B 17/863 606/309 |
| 2014/0045144 A1 | 2/2014 | Dukhan | |
| 2014/0163692 A1* | 6/2014 | Van Den Heuvel | A61N 1/36036 623/23.62 |
| 2014/0179985 A1 | 6/2014 | Andersson | |
| 2014/0277188 A1* | 9/2014 | Poulos | B65D 7/045 606/304 |
| 2014/0336447 A1* | 11/2014 | Bjorn | H04R 25/606 600/25 |
| 2015/0320523 A1* | 11/2015 | Way | A61C 8/0096 433/18 |

OTHER PUBLICATIONS

Supplemental Extended European Search Report in corresponding European Application No. 15836580.9, dated Jun. 28, 2018, 6 pages.

* cited by examiner

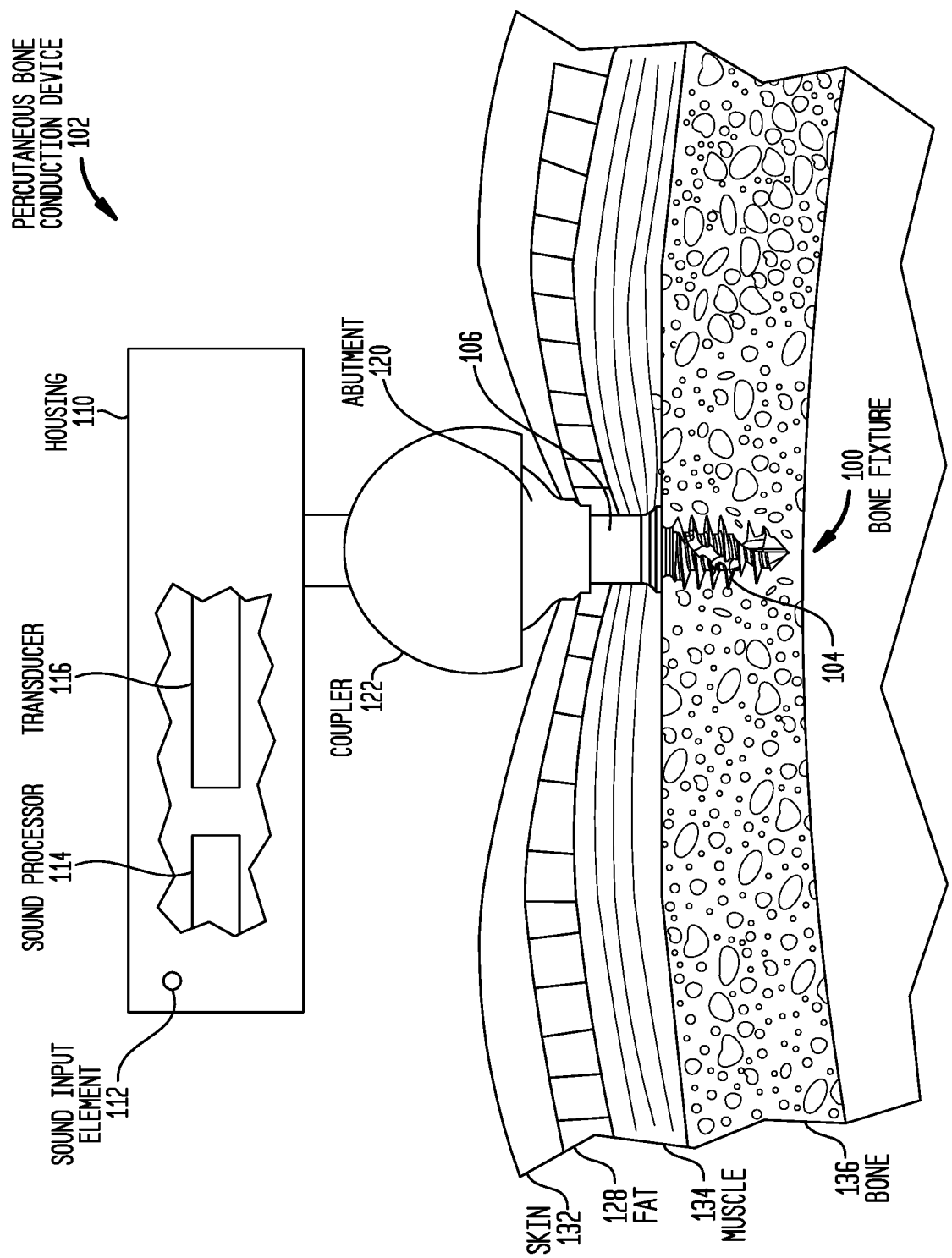

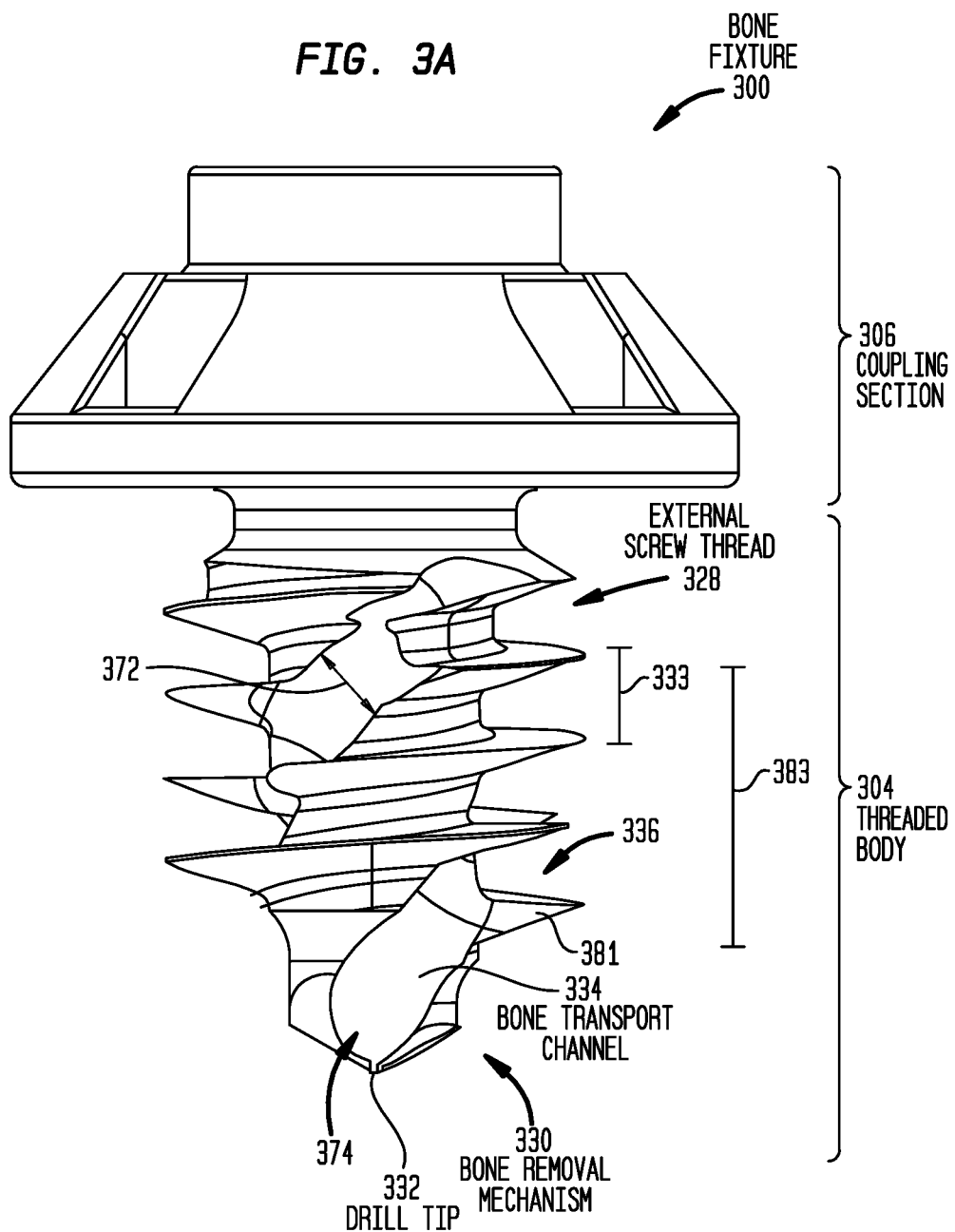

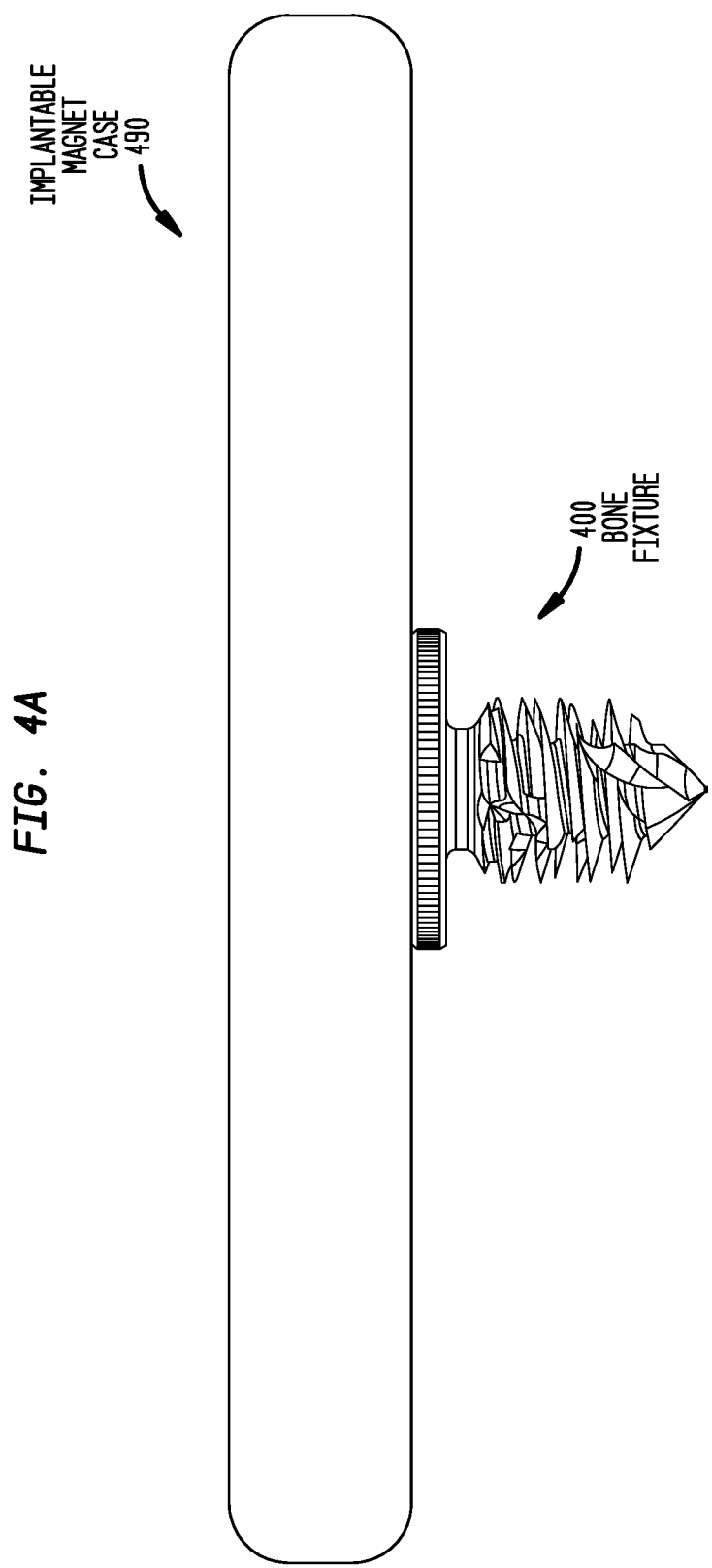

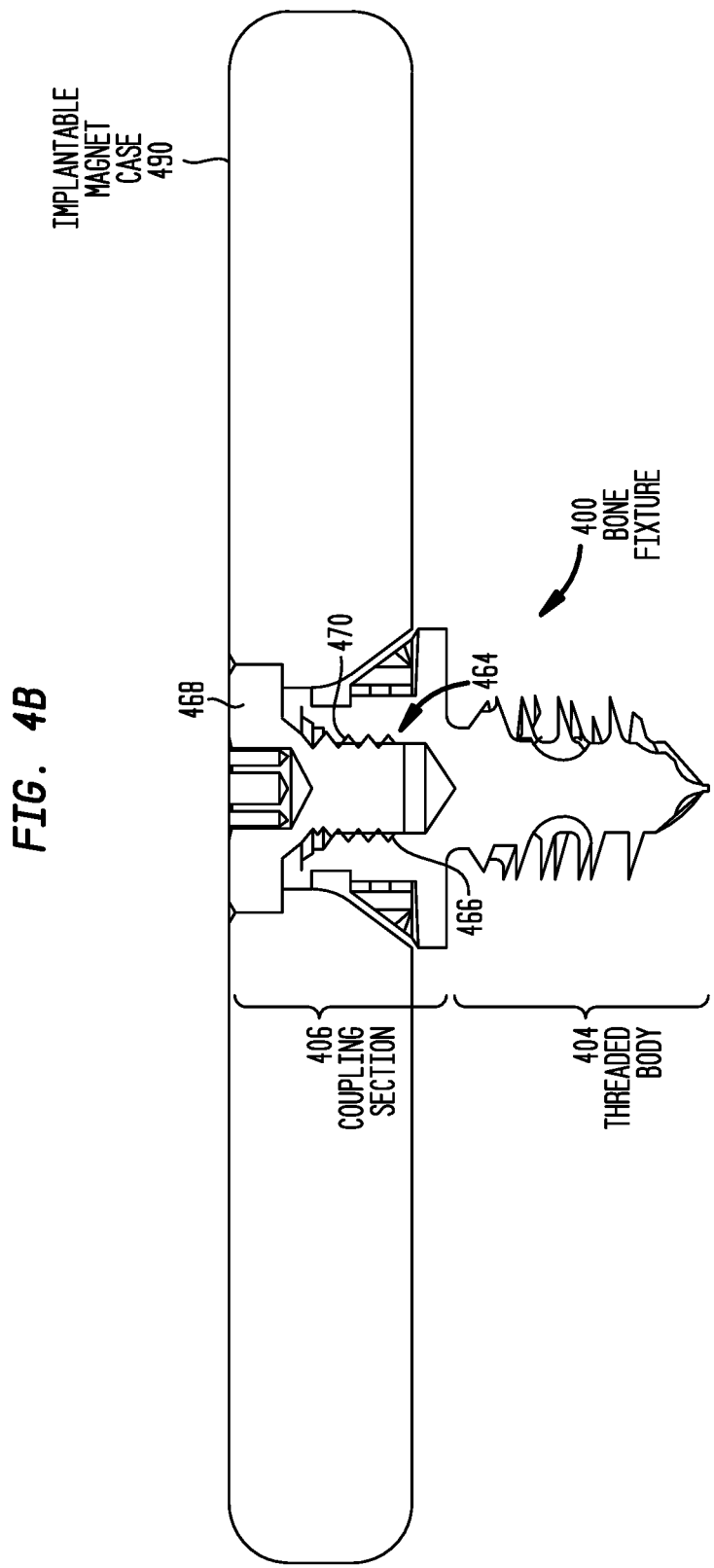

BONE FIXTURE FOR A MEDICAL PROSTHESIS

CROSS-REFERENCE TO RELATED APPLICATIONS

This application is a continuation application of U.S. patent application Ser. No. 14/837,091 entitled "Bone Fixture for a Medical Prosthesis," filed Aug. 27, 2015, which claims priority to U.S. Provisional Application No. 62/042,963 entitled "Bone Fixture for a Medical Prosthesis," filed Aug. 28, 2014. The content of these applications is hereby incorporated by reference herein.

BACKGROUND

Field of the Invention

The present invention relates generally to bone fixtures.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals suffering from conductive hearing loss typically receive an acoustic hearing aid. Hearing aids rely on principles of air conduction to transmit acoustic signals to the cochlea. Typically, a hearing aid is positioned in the ear canal or on the outer ear to amplify received sound. This amplified sound is delivered to the cochlea through the normal middle ear mechanisms resulting in the increased perception of sound by the recipient.

In contrast to acoustic hearing aids, certain types of implantable auditory prostheses, sometimes referred to as implantable acoustic auditory prostheses, convert a received sound into output mechanical force (vibration) for delivery to the recipient. The vibrations are transferred through the recipient's teeth, bone, and or other tissue to the cochlea. The vibrations cause movement of the cochlea fluid that generates nerve impulses resulting in perception of the received sound by the recipient. Acoustic auditory prostheses are suitable to treat a variety of types of hearing loss and may be prescribed for individuals who cannot derive sufficient benefit from acoustic hearing aids, cochlear implants, etc., or for individuals who suffer from stuttering problems. Implantable acoustic auditory prostheses include, for example, bone conduction devices, middle ear auditory prostheses (middle ear implants), direct acoustic stimulators (direct cochlear stimulators), or other partially or fully implantable auditory prosthesis that deliver vibrations to a recipient to directly or indirectly generate movement of the cochlea fluid.

SUMMARY

In one aspect of the present invention, a bone fixture for an auditory prosthesis is provided. The bone fixture comprises a self-drilling threaded body configured to be inserted into a recipient's bone and including a bone removal mechanism, and a coupling section attached to a proximal end of the threaded body that includes a connector interface located entirely proximal to the threaded body.

In another aspect of the present invention, an apparatus is provided. The apparatus comprises a body configured to be screwed into a recipient's bone, a coupling section attached to a proximal end of the body configured for attachment to a connector mechanism, a screw thread extending around the body, and a bone removal mechanism configured to form a hole in the recipient's bone.

BRIEF DESCRIPTION OF THE DRAWINGS

Embodiments of the present invention are described herein in conjunction with the accompanying drawings, in which:

FIG. 1 is a side view of a bone fixture in accordance with embodiments presented herein implanted in a recipient and attached to a percutaneous bone conduction device;

FIG. 3A is a side view of a bone fixture that includes a drill tip in accordance with embodiments presented herein;

FIG. 4A is a side view of a implantable magnet secured to a recipient with a bone fixture in accordance with embodiments presented herein; and FIG. 4B is a cross-sectional view of the implantable magnet and bone fixture of FIG. 4A.

DETAILED DESCRIPTION

Figure 2A:
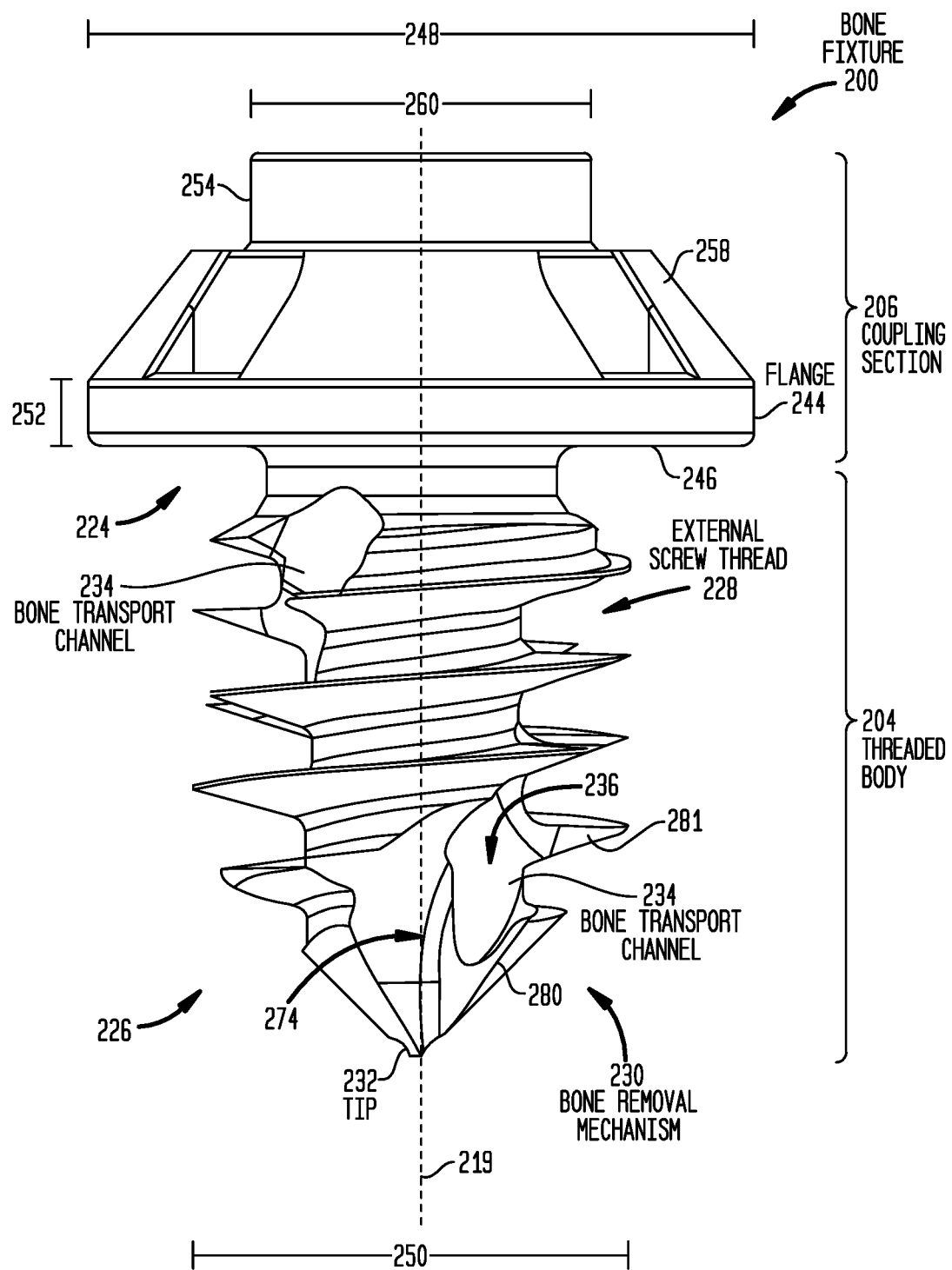
FIG. 2A is a side view of a bone fixture in accordance with embodiments presented herein.

Embodiments of the present invention are generally directed to a bone fixture for a medical prosthesis such as an implantable auditory prosthesis. The bone fixture includes a self-drilling threaded body that is configured to be inserted into a recipient's bone. The threaded body includes a bone removal mechanism configured to cut away parts of the bone that are in the path of the threaded body and to remove portions of the cut parts of the bone, sometimes referred to herein as bone fragments, from the hole. The bone fixture also comprises a coupling section that is attached to a proximal end of the threaded body. The coupling section is configured to be positioned external to the recipient's bone and includes a connector interface that is entirely/completely proximal to the threaded body.

There are different types of medical prostheses that may be partially or fully implanted into a recipient, including implantable auditory prostheses such as bone conduction devices (e.g., percutaneous, transcutaneous, transcutaneous active, etc.), middle ear auditory prostheses, direct acoustic stimulators, etc. It is to be appreciated that bone fixtures in accordance with embodiments presented herein may be used in connection with any of the above or other implantable auditory prostheses or other medical prostheses (e.g., facial prostheses). However, merely for ease of description, embodiments of the present invention are primarily described herein with reference to use of the bone fixture with bone conduction devices.

FIG. 1 is a cross-sectional view of a bone fixture 100 in accordance with embodiments presented herein. The bone fixture 100 is shown implanted in a recipient's bone 136 so as to couple a bone conduction device 102 to the recipient. As described further below, the bone fixture 100 comprises a self-drilling threaded body (shank) 104 that is configured to be inserted (e.g., screwed) into the recipient's bone 136. The bone fixture 100 also comprises a coupling section 106 that is attached to the proximal end of the threaded body 104.

The coupling section 106 is positioned entirely external to (i.e., outside of) the recipient's bone 136 and is configured for attachment to a connector mechanism. For example, the coupling section 106 includes a connector interface in the form of a threaded aperture (not shown in FIG. 1) that is configured to receive and mate with a threaded component of abutment 120. The bone fixture 100 is generally positioned below the recipient's skin 132 (e.g., adjacent to fat 128 and/or muscle 134). However, the abutment 120 extends through the recipient's skin 132. That is, the abutment 120 is a percutaneous abutment. As such, the bone conduction device 102 is sometimes referred to herein as a percutaneous bone conduction device 102 because the bone conduction device is attached to the recipient via the percutaneous abutment 102.

The percutaneous bone conduction device 102 comprises a housing 110 and a sound input element 112. The sound input element 112 may be, for example, a microphone, telecoil, audio input, etc. that is configured to receive and/or detect sound signals. In the embodiment of FIG. 1, sound input element 112 is located on housing 110. In alternative embodiments, the sound input element 112 may be positioned on a cable extending from housing 110, positioned in a recipient's ear, subcutaneously implanted in the recipient, etc. Additionally, multiple sound input elements 112 may also be provided.

Percutaneous bone conduction device 102 also comprises a sound processor 114, a transducer (actuator) 116, and/or various other operational components (not shown in FIG. 1) all disposed in housing 110. A portion of the housing 110 has been omitted from FIG. 1 to illustrate portions of the sound processor 114 and the transducer 116.

In operation, sound input element 112 converts received sound signals into electrical signals. These electrical signals are processed by the sound processor 114 to generate control signals that cause vibration of transducer 116. In other words, the transducer 116 converts the electrical signals received from the sound processor 114 into mechanical vibrations. The transducer 114 may be, for example, an electromagnetic transducer, piezoelectric transducer, etc.

Percutaneous bone conduction device 102 further includes a coupler 122 that is configured to be attached to the exposed portion of abutment 120 (i.e., the portion outside of the skin 132). The mechanical force generated by the transducer 110 is transferred through the coupler 122, abutment 120, and the bone fixture 100 to effect vibration of the recipient's skull bone 136 and eventual movement of fluid within the recipient's cochlea, thereby causing a hearing percept.

As noted above, FIG. 1 illustrates a percutaneous bone conduction device 102 that is attached to a recipient using a percutaneous abutment 120 and a bone fixture 100. It is to be appreciated that bone fixtures in accordance with embodiments presented herein, such as bone fixture 100, can be used with other types of bone conduction device devices, including passive and active transcutaneous bone conduction devices.

A passive transcutaneous bone conduction device utilizes an external transducer within an external component that is attached to a recipient using external and implantable magnetic plates. An active transcutaneous bone conduction device utilizes an implantable transducer that is directly or indirectly coupled to the recipient's bone. Bone fixtures in accordance with embodiments presented herein may be used to secure an implantable magnetic plate or an implantable transducer to a recipient.

Conventional percutaneous and transcutaneous bone conduction devices, including passive and active arrangements, utilize bone fixtures that require predrilling of a hole in the recipient's bone. That is, conventional bone fixtures require a surgeon to use a power drill to predrill holes for the bone fixtures and then to insert the bone fixtures into the predrilled holes. This necessarily requires a process where the surgeon drills into the recipient's skull bone to create the hole that will receive the bone fixture. More particularly, a surgeon typically first drills a relatively small guide or pilot hole in the bone and then uses a larger drill bit to widen the hole so as to receive a bone fixture. The need to drill a hole within the skull bone is a mental impediment that may prevent some potential recipient's from undergoing the needed surgical procedure for use of a bone conduction device.

As such, presented herein are bone fixtures that eliminate the need to predrill holes in a recipient's bone. More specifically, bone fixtures in accordance with embodiments presented herein are "self-drilling" in that the bone fixtures are configured to create/form a hole in the bone into which the threaded body 204 is inserted without the need for predrilling. That is, the self-drilling bone fixtures in accordance with embodiments presented herein perforate the surface of the recipient's bone and, during insertion, remove bone fragments from the recipient to form the hole into which the bone fixture is implanted. The self-drilling bone fixtures presented herein not only simplify the surgical procedure by removing two surgical steps (i.e., pilot hole drilling and widening drilling), but also makes the surgery less dramatic from a recipient perspective (i.e., the recipient no longer has to accept that the surgeon will use a power drill to drill a hole into the recipient's skull bone).

Figure 2B:
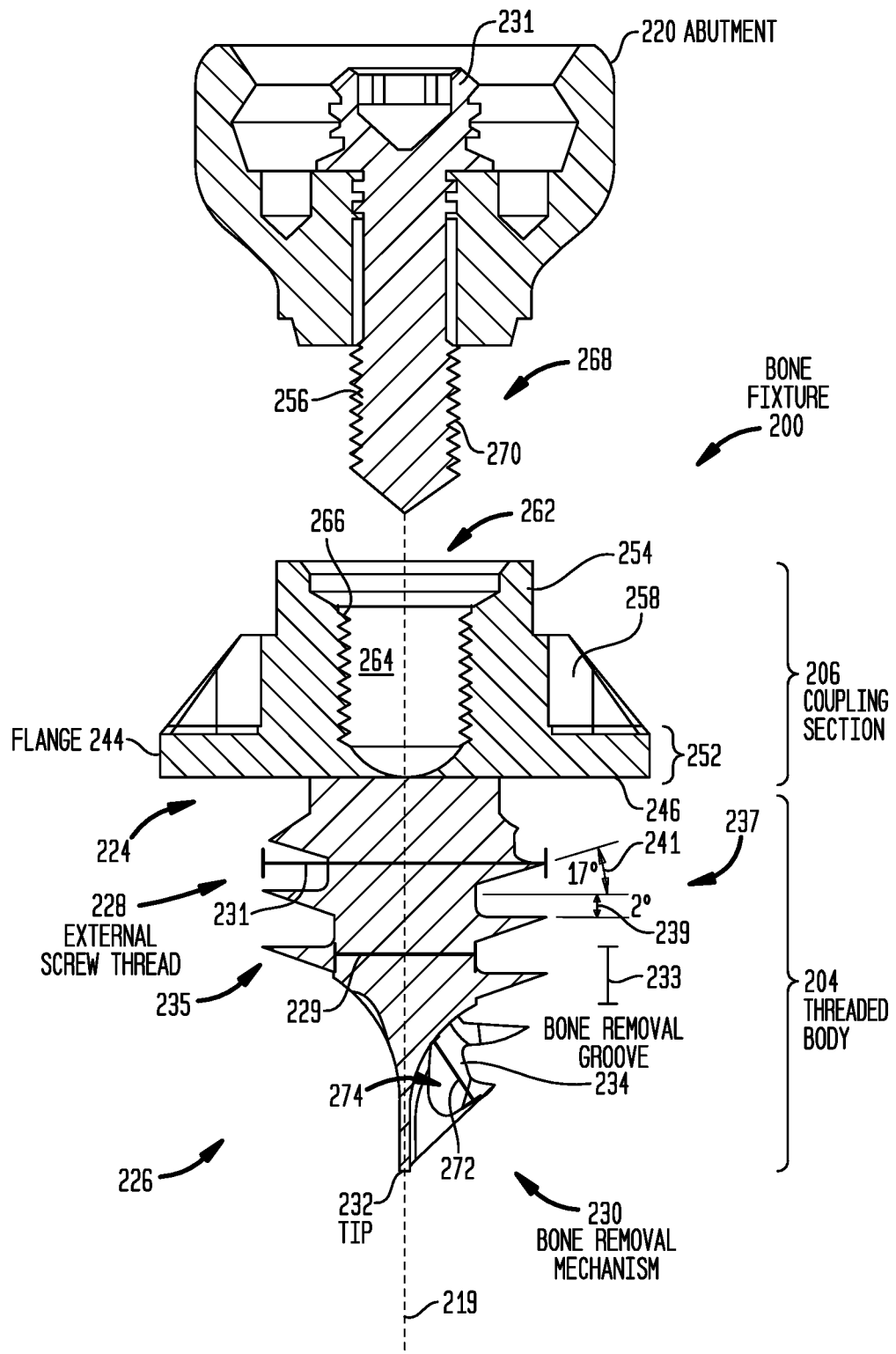
FIG. 2B is cross-sectional view of the bone fixture of FIG. 2A.
Figure 2C:
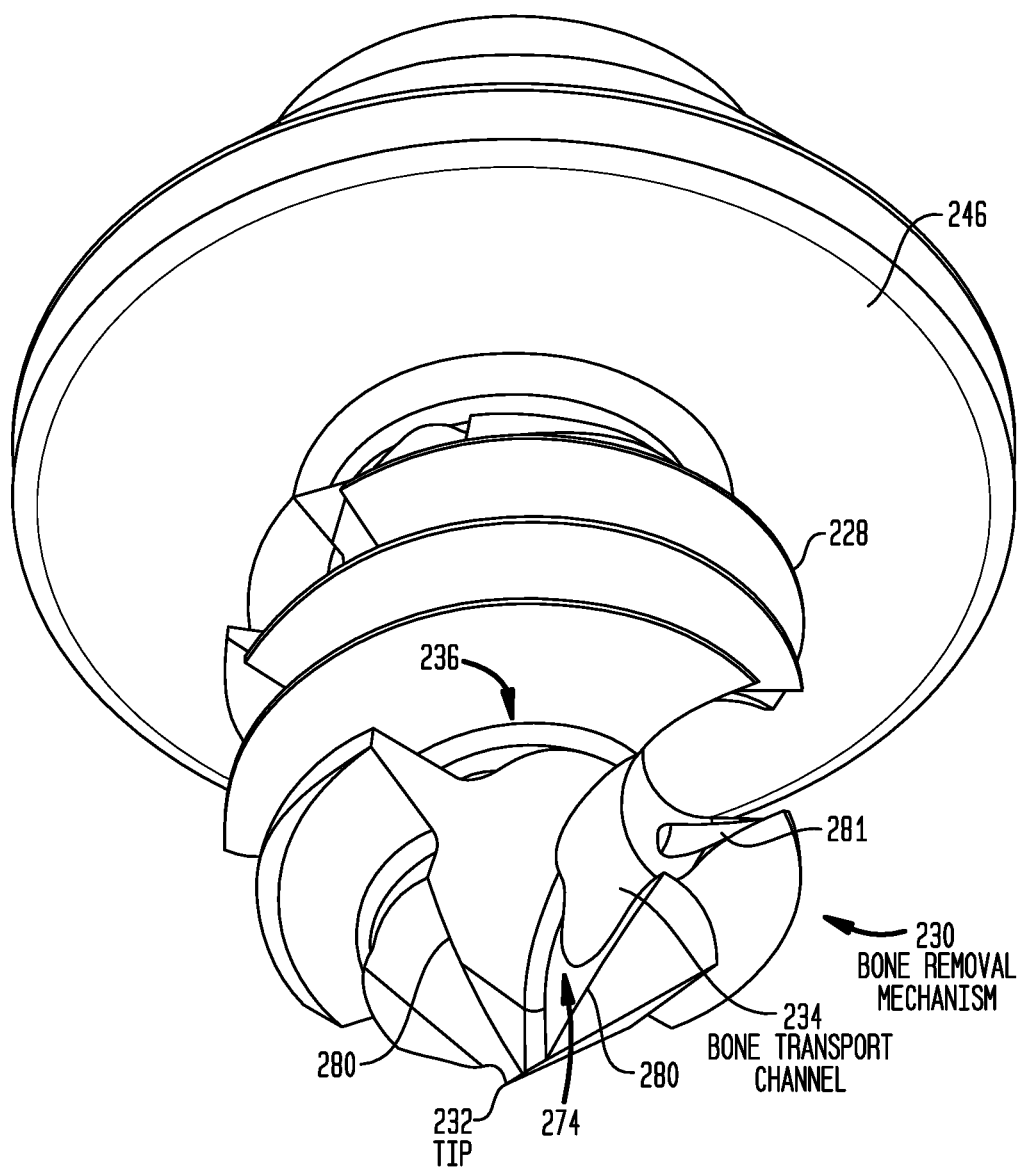
FIG. 2C is perspective view of the bone fixture of FIG. 2A.
Figure 2D:
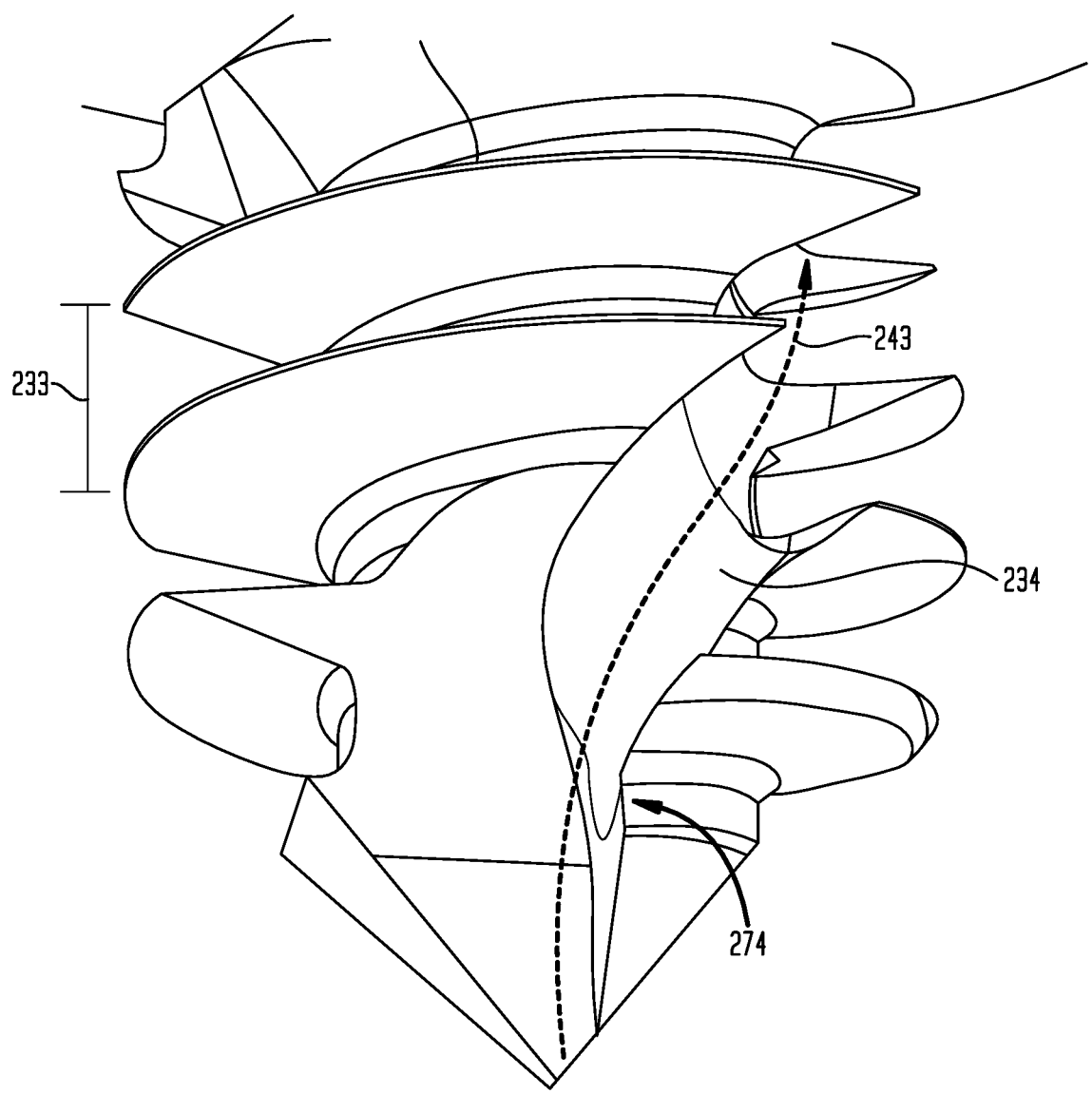
FIG. 2D is a schematic diagram illustrative the removal of bone fragments during insertion of the bone fixture of FIG. 2A.

FIG. 2A is a side view of a self-drilling bone fixture 200 in accordance with embodiments of the present invention. FIG. 2B is cross-sectional view of the bone fixture 200 and also illustrates a cross-sectional view of an abutment 220 that is configured to be mechanically coupled to the bone fixture 200. FIG. 2C is a perspective view of the bone fixture 200, while FIG. 2D is a schematic diagram illustrating operation of the self-drilling bone fixture 200 during insertion into the recipient's bone.

As shown, the bone fixture 200 comprises a threaded body 204, sometimes referred to herein as a threaded shank, that is configured to be inserted (i.e., screwed) into a recipient's bone. The threaded body 204 has a distal end 226 and a proximal end 224 that is attached to a coupling section 206. The distal end 226 is configured to be first inserted into the bone, while proximal end 224 is configured to be positioned adjacent the surface of the recipient's bone. For ease of illustration, the bone fixture 200 is shown in FIGS. 2A-2D prior to insertion into the recipient's bone.

The threaded body 204 includes an external/outer screw thread 228 that is configured to mate with the recipient's bone. The external screw thread 228 extends from adjacent the proximal end 224 to adjacent the distal end 226. Due to the presence of the external screw thread 228, the threaded body forms a male bone screw for installation in the recipient's bone.

As shown in FIG. 2B, in one specific embodiment the external screw thread 228 has a core/minor diameter 229 of approximately 1.5 millimeters (mm) and an outer/major diameter 231 of approximately 3.0 mm. The external screw thread 228 may also have a pitch 233 of approximately 0.6 mm. As used herein, the "pitch" refers to the linear distance between the same point of two adjacent turns. The external screw thread 228 further includes substantially sharp crests/tips 235 having, for example, a flat surface with a width of less than or equal to 0.05 mm. The substantially sharp crests increase the amount of bone that is positioned between the threads, thereby maximizing the strength of the bone that is used by the bone fixture 200 to drill into the skull. Additionally, the external screw thread 228 may have a thread angle 237 of approximately nineteen (19) degrees, with a leading flank angle 239 of approximately two (2) degrees and a following flank angle 241 of approximately seventeen (17) degrees. The larger flank angle 241 provides stability/support to the screw thread since the load forces are downwards on the thread as the bone fixture drills itself into the bone. In certain embodiments, the leading flank angle 239 and the following flank angle 241 may each have a tolerance of approximately +/−two (2) degrees without significantly affecting the self tapping/drilling performance of the bone fixture.

The threaded body 204 is a self-drilling and self-tapping screw/element that combines thrilling (threading and drilling, performed in the reverse order) action and actual insertion into a single driving step, instead of separate drilling, tapping, and installing steps. More specifically, the threaded body 204 is self-drilling because the threaded body includes a bone removal mechanism 230 configured to create/form a hole in the bone into which the threaded body 204 is inserted. To form the hole, the bone removal mechanism 230 is configured to perforate the bone and then to cut away parts of the bone that are in the path of the threaded body 204, thereby generating bone fragments. The bone removal mechanism 230 is further configured to remove a number of the bone fragments from the hole.

In the embodiments of FIGS. 2A-2D, the bone removal mechanism 230 comprises a distal cutting tip 232 that perforates the bone and that cuts the bone fragments as the threaded body 204 is advanced (turned) into the bone. The distal cutting tip 232 may have different arrangements but, in general, is significantly sharper than the tips of conventional bone fixtures that do not have the ability to perforate a recipient's bone. The distal cutting tip 232 also includes one or more cutting edges/surfaces 280 that are not included in conventional bone fixtures. As the threaded body 204 is turned into the bone, the cutting edge(s) 280 cut away the bone fragments to open up the hole. In the specific arrangement shown in FIGS. 2A-2C, the distal cutting tip 232 has a general conical shape and includes a distally facing point. The distal cutting tip 232 may be a nail point, a cone point, a Type 17 point, a Type 23 point, etc.

The bone removal mechanism 230 also comprises a bone transport channel 234. The bone transport channel 234 is an elongate groove that forms a discontinuity in the through the external screw thread 228, though bone transport channel 234 may make less than a complete turn around the threaded body 204. The bone transport channel 234 is sometimes referred to herein as being "transverse" to the external screw thread 228 because, as is evident from FIG. 2D, the bone transport channel 234 has a pitch that is substantially larger than the pitch 233 of the external screw thread 228. Therefore, the bone transport channel 234 extends angularly across the external screw thread 228. In one illustrative embodiment, the pitch of the transport channel is approximately 8 mm/revolution, while the pitch 233 of the external screw thread 228 is approximately 0.6 mm/revolution. external nal screw thread 228. The bone transport channel 234 follows a general helical path In operation, the bone transport channel 234 is configured to transport/channel bone fragments from the region of distal cutting tip 232 to an outer surface of the recipient's bone (i.e., out from the hole created by the bone fixture 200). More specifically, as noted above, the turning of the threaded body 204 into the bone causes the cutting edge(s) 280 to cut away bone fragments and thereby open up the hole. The cutting edge(s) 280 are positioned relative to the distal end 274 of the bone transport channel 234 such that a number of the bone fragments are collected by the distal end 274 of the bone transport channel 234. Again, as the threaded body 204 is turned, the bone fragments are forced through the bone transport channel 234 to the outer surface of the bone. FIG. 2D is a schematic diagram illustrating a path 243 for bone fragments through bone transport channel 234 to the outer surface of the bone.

The bone transport channel 234 may, in certain arrangements, extend from adjacent the distal cutting tip 232 to the base of the coupling section 206. In accordance with certain embodiments presented herein, the bone transport channel 234 has core diameter/width 272 that is less than or equal to the size of the bone fixture thread. The bone fixture thread size is the distance between the outer diameter (i.e., the crests 235) of the thread down to the core diameter (i.e., valley of the thread), not including the transport channel when those are intersecting). As such, there need not be a 1:1 ratio between the number of bone fragments that are cut and the number of bone fragments that are removed via the bone transport channel 234 as compression of some bone fragments and bone may be useful. For example, in one embodiment the external screw thread 228 has a pitch of approximately 0.8 mm and the bone transport channel 234 has core diameter/width 272 of approximately 0.7 mm.

As noted, in addition to being a self-drilling screw (i.e., having features that enable the formation of a hole in the recipient's bone), the threaded body 204 is also a self-tapping screw. That is, as the threaded body 204 is advanced into the hole created by the bone removal mechanism 230, the threaded body 204 is configured to "tap" the hole (i.e., the threaded body 204 is configured to further cut the bone at the outer surface of the hole to create an internal screw thread that mates with the external screw thread 228). In the embodiments of FIGS. 2A-2C, the threaded body 204 includes a relatively large discontinuity/gap 236 in the distal end of the external screw thread 228. The gap 236 forms a tap which creates the internal screw thread within the hole. More specifically, a portion 281 of the external screw thread 228 that is adjacent to the gap 236 forms the tap to create the internal screw thread within the bone hole. Portion 281 is the first part of the external screw thread 228 that contacts the bone as the bone fixture 200 is advanced into the bone.

In summary, it is to be appreciated that here there is a difference between the "drilling" and "tapping" features of bone fixture 200. In general, the drilling features create the core cavity (hole) into which the bone fixture 200 is inserted. The drilling is performed by, for example, parts 274, 230, 237, 280, 232, among others. In contrast, the tapping features are used to create the internal screw threads in the bone that mate with the external screw thread 228. Generally, portion 281 of the external screw thread 228 that comes in contact with the bone first is the part that performs the tapping. As noted above, a third component is the design of the external screw thread 228, namely the use of a following flank angle 241 that is substantially larger than the leading flank angle 239, which assists in driving the bone fixture 200 downwards into the bone as it is advanced into the bone.

As noted above, attached to the proximal end 224 of the threaded body 204 is a coupling section 206. The coupling section 206 includes a flange 244 that is configured to function as a stop mechanism when bone fixture 200 is installed into the bone. More specifically, the flange 244 has a substantially planar bottom surface 246 that is configured to be positioned adjacent to (e.g., abut/contact) the top surface of the recipient's bone when the bone fixture 200 is inserted into the recipient's bone. As such, the flange 244 may prevent the bone fixture 200 from potentially penetrating completely through the recipient's bone.

Flange 244 may have a diameter 248 that is greater than or equal to the maximum outer diameter 250 of the external screw thread 228. Although flange 244 is illustrated in FIGS. 2A-2C as being circular, flange 244 can be configured in a variety of shapes. Also, the diameter and thickness 252 of flange 244 can vary depending on, for example, the particular intended application of the bone fixture 200.

The coupling section 206 further includes an elongate central member 254 extending proximally from the flange 244. An optional outer member 258 surrounds a portion of the elongate central member 254. The elongate central member 254 may have, for example, a circular, oval, protruding or recessed hex, or another other multi-lobe cross-sectional shape that lies on a plane normal to a central longitudinal axis 219 of the bone fixture 200. That is, elongate central member 254 may have an elongate tubular, hexagonal, or other shape. In general, the elongate central member 254 has a diameter 260 that is less than or equal to the diameter 248 of the flange 244.

In certain embodiments, the elongate central member 254 and/or the outer member 258 include features that mate with a tool for installation of the bone fixture 200 in to the recipient's bone. For example, in an exemplary embodiment the elongate central member 254 has a hexagonal cross-sectional shape such that a female hex-head socket wrench can be used to apply torque to the bone fixture 200. In other embodiments, the elongate central member 254 has a tubular shape (i.e., circular cross-section) and thus does not have a protruding hex for engagement with a hex-head socket. In such embodiments, the outer member 258 may include the features that are configured to engage with an installation tool.

Disposed in the elongate central member 254 is a connector interface 262 that is configured for mechanical attachment to a connector mechanism of, for example, an abutment, implantable magnet, implantable vibrator, etc. In the embodiment of FIGS. 2A-2C, the connector interface 262 is a threaded aperture 264 with an internal screw thread 266 configured to mate with the external screw thread on a connector mechanism.

FIG. 2B illustrates an example connector mechanism 268 that forms part of a screw 231 of a percutaneous (i.e., skin-penetrating) abutment 220. The connector mechanism 268 is a threaded body 256 with an external screw thread 270. In operation, the connector mechanism 268 is threaded into connector interface 262 so that external screw thread 270 mates with internal screw thread 266, thereby rigidly attaching abutment 220 to the bone fixture 200. The rigid attachment between the abutment 220 and the bone fixture 200 enables the transfer of vibrations from a percutaneous bone device to the recipient's bone so as to evoke a hearing percept.

As noted above, the connector interface 262 is a screw interface (i.e., includes an internal screw thread 266 for mating with an external screw thread of a connector mechanism). It is also to be appreciated that the use of a screw interface is illustrative and that other types of connector interfaces could be used in alternative embodiments. Furthermore, it is to be appreciated that the connection of connector interface 262 to a percutaneous abutment 220 is also merely illustrative. The connector interface 262 could alternatively be attached to a connector mechanism of, for example, an abutment, implantable magnet, implantable vibrator, etc. (i.e., the bone fixture 200 in accordance with embodiments of the present invention may be used in both percutaneous and transcutaneous arrangements).

In the embodiments of FIGS. 2A-2D, the coupling section 206 in general, and the connector interface 262 in particular, is entirely proximal to the threaded body 204. That is, although the coupling section 206 is attached to the threaded body 204, no portion of the connector interface 262 or other part of the coupling section 206 extends into the threaded body 204 (i.e., the coupling section 206 terminates at the bottom surface 246 of the flange 244). In this way, when the bone fixture 200 is inserted into the recipient's bone, the entirety of the coupling section 206 is proximal to (i.e., external or outside) the recipient's bone.

As noted above, the threaded body 204 is self-drilling so as to remove bone from the recipient as the threaded body is advanced into the bone (i.e., no hole is drilled into the bone before the threaded body 204 is inserted). In order to reduce the amount of bone that is removed during insertion, the threaded body 204 may have a diameter that is significantly smaller than conventional bone fixtures that are not self-drilling. More specifically, since conventional bone fixtures are not self-drilling, the diameter of such conventional bone fixtures is selected to, for example, merely ensure that the bone fixture remains securely within the bone. In order to prevent the possibility of breakage, conventional bone fixtures are intentionally made with a large diameter that accommodates a significant part of the connector interface for attachment to a connector mechanism of an abutment, magnet, etc.

However, as noted, a self-drilling bone fixture removes the bone as it is advanced into the recipient's bone and the thinner the threaded body, the less bone that is removed. Accordingly, the diameter of the threaded body 204 of FIGS. 2A-2D is minimized through placement of the connector interface 262 entirely outside of the threaded body 204. In certain embodiments, the diameter of threaded body 204 is approximately 3 mm, which is substantially smaller (e.g., approximately 33% smaller) than a 4.5 mm diameter of conventional bone fixtures that include all or part of the connector interface within the threaded body. If a substantially thin threaded body, such as that shown in FIGS. 2A-2D, were used with a conventional arrangement in which part of all of the connector interface is within the threaded body, the threaded body would be susceptible to strain and potential breakage during insertion (e.g., breakage resulting from the existence of thin walls within a threaded body that includes all of part of a conventional connector interface).

The threaded body 204 and coupling section 206 may be formed as a unitary piece (e.g., the bone fixture 200 is formed from a single piece of material in a monolithic structure). Bone fixture 200 can also be formed from a material that has the ability to integrate into surrounding bone tissue (i.e., may be formed from a material that exhibits acceptable osseointegration characteristics). In one embodiment, the bone fixture 200 is formed from titanium. Additionally, the bone fixture 200 or portions thereof may include a coating, such as Hydroxyapatite, to facilitate osseointegration.

In general, the threaded body 204 has a length that is sufficient to securely anchor the bone fixture 200 to the recipient's bone without penetrating entirely through the bone. The length of the body can therefore depend, for example, on the thickness of the bone (e.g., skull) at the implantation site and/or the intended application. As such, the dimensions of the various features of the bone fixture 200 may also vary.

The bone fixture 200 shown in FIGS. 2A-2D is illustrative and bone fixtures in accordance with embodiments of the present invention may have different sizes and/or configurations. For example, FIG. 3A illustrates a bone fixture 300 that includes a different distal cutting tip than the tip shown in the arrangement of FIGS. 2A-2D.

More specifically, the bone fixture 300 of FIG. 3A includes a threaded body 304 and a coupling section 306. The coupling section 306 is substantially the same as coupling section 206 of FIGS. 2A-2D and, as such, is not described further herein.

The threaded body 304, which is configured to be screwed into a recipient's bone, comprises an external/outer screw thread 328 configured to mate with the recipient's bone. Similar to the embodiment of FIGS. 2A-2D, the threaded body 304 is a self-drilling and self-tapping screw. The threaded body 304 is self-drilling because the threaded body includes a bone removal mechanism 330 that is configured to form a hole in the bone into which the threaded body 304 is inserted. To form the hole, the bone removal mechanism 330 cuts away bone fragments and removes the bone fragments from the created hole.

Figure 3B:
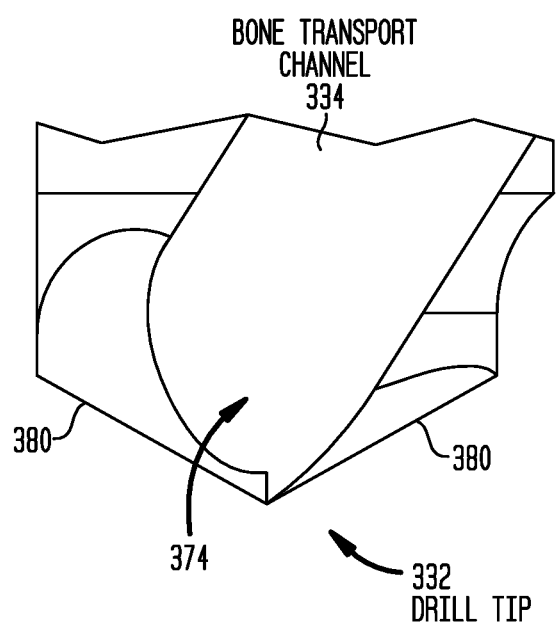
FIG. 3B is enlarged view of the drill tip shown in FIG. 3A.
Figure 3C:
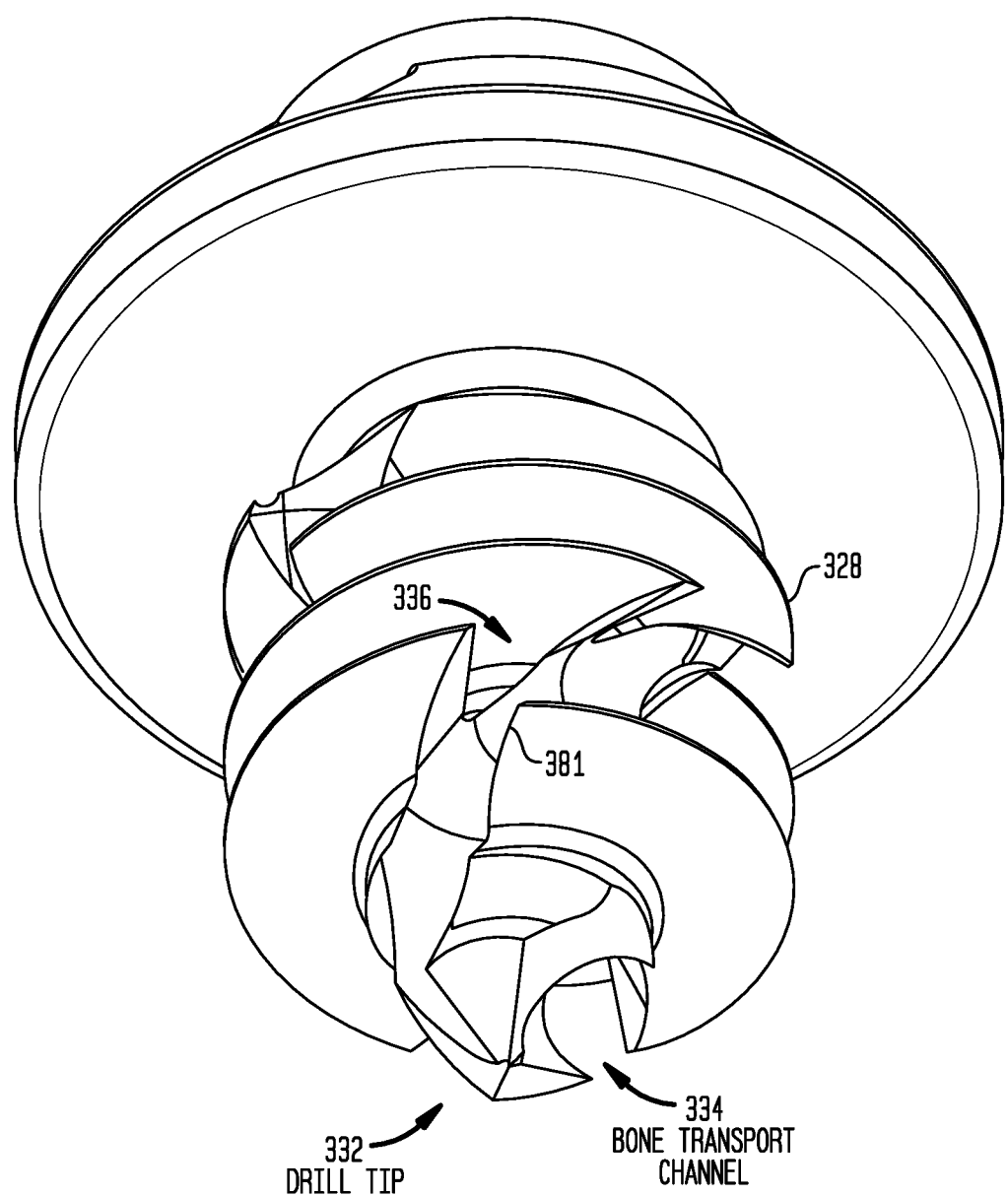
FIG. 3C is a perspective view of the drill tip shown in FIG. 3A.

In the embodiment of FIG. 3A, the bone removal mechanism 330 comprises a distal cutting tip 332 that is configured to perforate the bone and to cut away the bone fragments as the threaded body 304 is advanced (turned) into the bone. The distal cutting tip 332 of FIG. 3A is a drill tip/point, namely a twist drill bit tip with multiple cutting edges 380. FIG. 3B is an enlarged side view of the twist drill bit tip 332 of FIG. 3A, while FIG. 3C is a bottom perspective view of the twist drill bit tip 332.

The bone removal mechanism 330 also comprises a bone transport channel 334. The bone transport channel 334 is an elongate groove that forms a discontinuity in the external screw thread 328. The bone transport channel 334 follows a general helical path through the external screw thread 328 and is generally transverse to the external screw thread 328 (i.e., has a pitch 383 that is substantially larger than the pitch 333 of the external screw thread 328). Therefore, the bone transport channel 334 extends angularly across the external screw thread 328.

The bone transport channel 234 may, in certain arrangements, extend from adjacent the distal cutting tip 332 to the base of the coupling section 306. In accordance with certain embodiments presented herein, the bone transport channel 234 has core diameter/width 372 that is less than or equal to the thread pitch 333.

In operation, the bone transport channel 334 is configured to transport/channel bone fragments from the region of twist drill bit tip 332 to an outer surface of the recipient's bone (i.e., out from the hole created by the bone fixture 300). More specifically, the turning of the threaded body 304 into the bone causes the cutting edge(s) 380 of the twist drill bit tip 332 to cut away bone fragments and thereby open up the hole. The cutting edge(s) 380 are positioned relative to the distal end 374 of the bone transport channel 334 such that a number of the bone fragments are collected by the distal end 374. Again, as the threaded body 304 is turned, the bone fragments are forced through the bone transport channel 334 to the outer surface of the bone.

In addition to being a self-drilling screw (i.e., having features that enable the formation of a hole in the recipient's bone), the threaded body 304 is also a self-tapping screw. That is, as the threaded body 304 is advanced into the hole created by the bone removal mechanism 330, the threaded body 304 is configured to tap the hole (i.e., further cut the bone at the outer surface of the hole to create an internal screw thread that mates with the external screw thread 328). In the embodiments of FIGS. 3A and 3B, the threaded body 304 includes a discontinuity/gap 336 in the distal end of the external screw thread 328. The gap 336 operates as a tap that creates the internal screw thread within the hole. More specifically, a portion 381 of the external screw thread 328 that is adjacent to the gap 336 forms the tap to create the internal screw thread within the bone hole. Portion 381 is the first part of the external screw thread 328 that contacts the bone as the bone fixture 300 is advanced into the bone.

In summary, it is to be appreciated that here is a difference between the "drilling" and "tapping" features of bone fixture 300. In general, the drilling features create the core cavity (hole) into which the bone fixture 200 is inserted. In contrast, the tapping features are used to create the internal screw threads in the bone that mate with the external screw thread 328.

Embodiments of the present invention have been primarily described herein with reference to bone fixtures for attachment to a percutaneous abutment. However, as noted above, it is to be appreciated that these embodiments are merely illustrative and bone fixtures in accordance with embodiments of the present invention may be used to, for example, secure an implantable transducer to the recipient's bone, secure an implantable magnetic plate to a recipient's bone, etc. For example, FIGS. 4A and 4B are side and cross-sectional views, respectively, of an implantable magnet case 490 that is configured to have one or more magnets (not shown in FIGS. 4A and 4B) positioned therein. The implantable magnet case 490 is attached to a bone fixture 400 that is configured to be inserted into a recipient's skull.

The bone fixture 400 includes a threaded body 404 and a coupling section 406. The threaded body 404 may be, similar to the threaded bodies 204 or 304 described above, a self-cutting and self-tapping element for insertion into the recipient's bone without the need to first drill a hole. The coupling section 406 is configured for attachment to the implantable magnet case 490. More specifically, the coupling section 406 includes a connector interface in the form of a threaded aperture 464 with an internal screw thread 466 configured to mate with an external screw thread 470 of a connector mechanism 468 of the implantable magnet case 490. In operation, the connector mechanism 468 is threaded into aperture 464 so that external screw thread 470 mates with internal screw thread 466, thereby rigidly attaching the implantable magnet case 490 to the bone fixture 400.

It is to be appreciated that the above embodiments are not mutually exclusive and may be combined with one another in various arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A bone fixture, comprising:
a self-drilling threaded body configured to be inserted into a recipient's bone and including a bone removal mechanism, wherein an external screw thread extends from adjacent a proximal end of the self-drilling threaded body to adjacent a distal end of the self-drilling threaded body; and
a coupling section attached on a distal end of the coupling section to the proximal end of the self-drilling threaded body, wherein the coupling section includes a connector interface, and wherein the connector interface is located entirely proximal to the threaded body and is configured to couple with a connector mechanism to be attached to the recipient's bone on a proximal end of the coupling section.

2. The bone fixture of claim 1, wherein the bone removal mechanism includes a distal cutting tip configured to form a hole in the bone into which the threaded body is inserted without the need for predrilling of the hole.

3. The bone fixture of claim 2, wherein the distal cutting tip is configured to perforate the recipient's bone and includes one or more cutting edges configured to cut bone fragments from the recipient's bone.

4. The bone fixture of claim 3, wherein the distal cutting tip of the threaded body has a conical shape and includes a distally facing point.

5. The bone fixture of claim 3, wherein the distal cutting tip is a twist drill bit tip.

6. The bone fixture of claim 1, wherein the bone removal mechanism includes a bone transport channel comprising:
a groove extending along a surface of the threaded body from a cutting tip to adjacent the coupling section, wherein the groove is transverse to and extends through the external screw thread.

7. The bone fixture of claim 6, wherein the bone transport channel has a constant width that is less than a pitch of the external screw thread.

8. The bone fixture of claim 7, wherein the threaded body includes a tap to create an internal screw thread within a hole that is configured to mate with the external screw thread.

9. The bone fixture of claim 8, wherein the tap is formed by a distal end of the bone transport channel.

10. The bone fixture of claim 1, wherein the coupling section comprises:
a flange attached to the threaded body; and
an elongate central member extending proximally from the flange, wherein the elongate central member has outer dimensions that are less than or equal to outer dimensions of the flange.

11. A bone fixture, comprising:
a body configured to be screwed into a recipient's bone, wherein the body comprises an external screw thread that extends from adjacent a proximal end of the body to adjacent a distal end of the body;
a coupling section attached on a distal end of the coupling section to the proximal end of the body, wherein the coupling section is located entirely proximal relative to the body and includes a connector interface which is configured for attachment to a connector mechanism to be attached to the recipient's bone on a proximal end of the coupling section;
a screw thread extending around the body; and
a bone removal mechanism configured to form a distally extending hole in the recipient's bone.

12. The bone fixture of claim 11, wherein the bone removal mechanism includes a distal cutting tip.

13. The bone fixture of claim 12, wherein the distal cutting tip is configured to perforate the recipient's bone and includes one or more cutting edges configured to cut bone fragments from the recipient's bone.

14. The bone fixture of claim 12, wherein the distal cutting tip of the body has a conical shape and includes a distally facing point.

15. The bone fixture of claim 12, wherein the distal cutting tip is a twist drill bit tip.

16. The bone fixture of claim 11, wherein the bone removal mechanism includes a bone transport channel comprising:
a groove extending along a surface of the body from a cutting tip to adjacent the coupling section, wherein the groove is transverse to and extends through the external screw thread.

17. The bone fixture of claim 16, wherein the bone transport channel has a constant width that is less than a pitch of the external screw thread.

18. The bone fixture of claim 16, wherein the body includes a tap to create an internal screw thread within the hole that is configured to mate with the external screw thread.

19. The bone fixture of claim 18, wherein the tap is formed by a distal end of the bone transport channel.

20. The bone fixture of claim 11, wherein the coupling section comprises:
a flange attached to the body; and
an elongate central member extending proximally from the flange, wherein the elongate central member has outer dimensions that are less than or equal to the outer dimensions of the flange.

* * * * *